United States Patent [19]

Gerecke et al.

[11] 4,100,173

[45] Jul. 11, 1978

[54] DIBENZ[B,F]OXEPIN DERIVATIVES

[75] Inventors: Max Gerecke; Emilio Kyburz, both of Reinach, Switzerland; Jean-Pierre Kaplan, Le Plessis Robinson, France

[73] Assignee: Hoffmann-La Roche Inc., Nutley, N.J.

[21] Appl. No.: 778,897

[22] Filed: Mar. 18, 1977

Related U.S. Application Data

[62] Division of Ser. No. 534,033, Dec. 18, 1974, Pat. No. 4,032,525.

[30] Foreign Application Priority Data

Jan. 4, 1974 [CH] Switzerland .............................. 62/74
Nov. 20, 1974 [CH] Switzerland ........................ 15369/74

[51] Int. Cl.² .......................................... C07D 313/14
[52] U.S. Cl. .................................................. 260/333
[58] Field of Search .......................................... 260/333

[56] References Cited

FOREIGN PATENT DOCUMENTS 1,558,916 1/1969 France.
2,151,568 4/1973 France.

OTHER PUBLICATIONS

Chemical Abstracts, vol. 72 (1970) 55288s.
Chemical Abstracts, vol. 72 (1970) 55223s.
Chemical Abstracts, vol. 79 (1973) 92282a.

*Primary Examiner*—Norma S. Milestone
*Attorney, Agent, or Firm*—Samuel L. Welt; George M. Gould; William G. Isgro

[57] ABSTRACT

Dibenz[b,f]oxepins of the formula

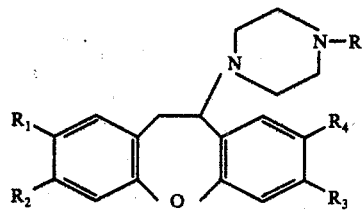

I wherein R, $R_1$, $R_2$, $R_3$ and $R_4$ are as hereinafter described, are described. The foregoing compounds exhibit strong central depressant and neuroleptic properties, and are useful, for example, in the treatment of acute or chronic schizophrenia and also as tranquilizers.

2 Claims, No Drawings

DIBENZ[B,F]OXEPIN DERIVATIVES

This is a division of application Ser. No. 534,033 filed Dec. 18, 1974, now U.S. Patent No. 4,032,525, issued June 28, 1977.

BRIEF SUMMARY OF THE INVENTION

The dibenz[b,f]oxepin derivatives of the invention are compounds of the formula

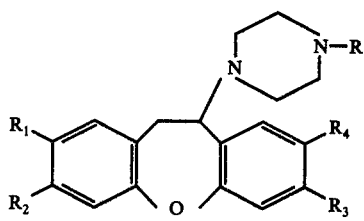

I wherein R is lower alkyl, lower alkenylalkyl, lower alkynylalkyl, which may be substituted by cyano, hydroxy or alkanoyloxy, when other than methyl, or a group of the formula

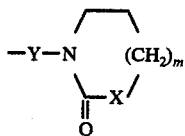

(a)

wherein X is oxygen, sulfur, imino, lower alkylimino or methylene, Y is ethylene or propylene which may be substituted by lower alkyl and $m$ is zero or 1; one of $R_1$ and $R_2$ is hydrogen and the other is halogen, lower alkyl, lower alkoxy, lower alkylthio, trifluoromethyl or hydroxy; and one of $R_3$ and $R_4$ is hydrogen and the other is hydrogen, halogen, lower alkyl, lower alkoxy, lower alkylthio, trifluoromethyl or hydroxy, or pharmaceutically acceptable acid addition salts thereof.

DETAILED DESCRIPTION OF THE INVENTION

The dibenz[b,f]oxepin derivatives of the invention are compounds of the formula

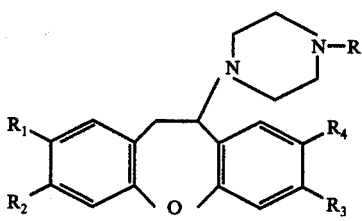

I wherein R is lower alkyl, lower alkenyl, lower alkynyl, cyano-lower alkyl of 3-7 carbon atoms, hydroxy-lower alkyl of 2-6 carbon atoms, alkanoyloxy-lower alkyl with 2-6 carbon atoms in the lower alkyl moiety, cyano-lower alkenyl alkyl, hydroxy-lower alkenyl-alkyl, alkanoyloxy-lower alkenyl-alkyl, cyano-lower alkynyl-alkyl, hydroxy-lower alkynyl-alkyl, alkanoyloxy-lower alkynyl-alkyl, or R is a group of the formula

(a)

wherein X is oxygen, sulfur, imino, lower alkylimino or methylene, Y is ethylene or propylene which may be substituted by lower alkyl and $m$ is zero or 1; one of $R_1$ and $R_2$ is hydrogen and the other is halogen, lower alkyl, lower alkoxy, lower alkylthio, trifluoromethyl or hydroxy; and one of $R_3$ and $R_4$ is hydrogen and the other is hydrogen, halogen, lower alkyl, lower alkoxy, lower alkylthio, trifluoromethyl or hydroxy, or pharmaceutically acceptable addition salts thereof.

As used herein, the term "lower alkyl", alone or in combination with other groups, denotes straight-chain or branched-chain aliphatic groups which, unless otherwise described, preferably contain from 1 to 6 carbon atoms, for example, methyl, ethyl, isopropyl, n-hexyl and the like. The term "lower alkoxy" denotes an alkyl ether group in which the lower alkyl group is as described above, for example, methoxy, ethoxy, propoxy, pentoxy, and the like. The terms "lower alkenyl alkyl" and "lower alkynyl alkyl" mean that the lower alkenyl and lower alkynyl are each linked via an alkyl (alkylene) group, i.e., at least via a methyl (methylene) and denote straight-chain or branched-chain groups and preferably contain from 3 to 6 carbon atoms, for example, allyl, 2-butenyl or 2,4-pentadienyl and 2-propynyl or 2-butynyl. The term "alkanoyloxy" denotes a straight-chain or branched-chain group which contains from 2 to 18 carbon atoms, for example, acetoxy, pivaloyloxy, n-pentanoyloxy, and the like. Preferred alkanoyloxy groups are those which contain from 6 to 18 carbon atoms, for example, hexanoyloxy, heptanoyloxy, octanoyloxy, nonanoyloxy, decanoyloxy, undecanoyloxy, dodecanoyloxy, tetradecanoyloxy, hexadecanoyloxy, octadecanoyloxy, and the like. The term "halogen" denotes fluorine, chlorine, bromine and iodine; chlorine is preferred.

The dibenz[b,f]oxepin derivatives of the invention, that is, the compounds of formula I and their pharmaceutically acceptable acid addition salts exhibit strong central depressant and neuroleptic properties, and can be used, for example, in the treatment of acute or chronic schizophrenia and also as tranquilizers. Advantageously, in certain derivatives of the invention, cataleptic side-effects are observed only to slight extent, i.e., only insignificant motor disorders occur. More particularly, this advantage is present in those compounds of formula I in which R is cyanoethyl or a group of formula (a), especially the group of the formula

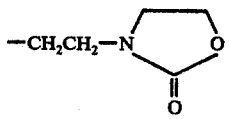

and their pharmaceutically acceptable acid addition salts. Such derivatives are therefore preferred. Especially preferred derivatives are 3-{4-[2-chloro-10,11-dihydro-dibenz[b,f]oxepin-10-yl]-1-piperazinyl}-propionic acid nitrile, 3-[2-{4-[10,11-dihydro-2,8-dimethyldibenz[b,f]oxepin-10-yl]-1-piperazinyl}-ethyl]-2-oxazolidinone, 3-[2-{4-[8-fluoro-10,11-dihydro-2-methyl-dibenz[b,f]oxepin-10-yl]-1-piperazinyl}-ethyl]-2-oxazolidinone and 3-[2-{4-[2-chloro-10,11-dihydro-dibenz[b,f]oxepin-10-yl]-1-piperazinyl}-ethyl]-2-oxazolidinone and their pharmaceutically acceptable acid addition salts.

The dibenz[b,f]oxepin derivatives, that is, the compounds of formula I of the invention and their salts, can be prepared by the following processes:

(a) reacting a compound of the formula

II wherein Z is a leaving atom or group and $R'_1$-$R'_4$ have the values accorded to $R_1$-$R_4$ hereinbefore but wherein any hydroxy group(s) present can be protected, with a compound of the formula wherein R is as earlier described, (b) reducing a compound of the formula

IV wherein R and $R'_1$-$R'_4$ are as earlier described, or (c) reacting a compound of the formula

V wherein $R'_1$-$R'_4$ are as earlier described, with a compound yielding the group R, or (d) for the preparation of a compound of formula I wherein R is alkanoyloxy-lower alkyl, alkanoyloxy-lower alkenyl alkyl or alkanoyloxy-lower alkynyl alkyl, reacting a compound of the formula

VI wherein $R'_1$-$R'_4$ is as earlier described and R' is hydroxy-lower alkyl, hydroxy-lower alkenyl alkyl or hydroxy-lower alkynyl alkyl, with an alkanecarboxylic acid or a reactive derivative thereof,
or (e) for the preparation of a compound of formula I wherein R is lower alkyl or hydroxy-lower alkyl, reducing a compound of the formula

VII wherein $R'_1$-$R'_4$ are as earlier described and $R_5$ is lower alkanoyl, hydroxy-lower alkanoyl or lower alkoxycarbonyl, and converting any protected hydroxy group(s) denoted by $R'_1$-$R'_4$ into hydroxy group(s) if necessary and, if desired, converting a product obtained into a pharmaceutically acceptable acid addition salt.

The leaving atom or group denoted by Z in the starting materials of formula II is preferably halogen or alkyl-substituted or aryl-substituted sulfonyloxy. The alkyl group present in the leaving group is preferably lower alkyl, especially methyl, the aryl group present in the leaving group is preferably phenyl or tolyl. When Z is halogen, chlorine or bromine is preferred.

The starting materials of formula II can be prepared according to known methods. For example, the starting materials of formula II wherein Z is as earlier described, can be prepared as follows:

When Z is halogen, a corresponding 10-oxo compound is converted by reduction, for example, using sodium borohydride, into the 10-hydroxy compound which is then reacted with a suitable halide, for example, thionyl chloride or thionyl bromide, or with a hydrohalide in the presence of a water-binding agent, for example, hydrogen chloride and calcium chloride.

When Z is alkyl-substituted or aryl-substituted sulfonyloxy, a corresponding 10-hydroxy compound is reacted with an alkyl-substituted or aryl-substituted sulfonic acid halide, for example, the chloride.

The starting materials of formula III can be prepared, for example, as set forth below, wherein Z and R are as previously described and $R_6$ is a suitable protecting group, for example, benzyl or lower alkoxycarbonyl, such as, methoxycarbonyl or ethoxycarbonyl.

More particularly, the compounds of formula III are prepared by the condensation of a compound of the formula

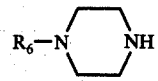

VIII with a compound of the formula

Z—R        IX which is preferably carried out in the presence of an acid-binding agent, for example, potassium carbonate or triethylamine. The protecting group denoted by $R_6$ is subsequently removed from the condensation product of the formula

X and yields the compound

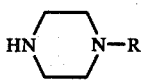

III

The benzyl group can be removed by hydrogenolysis and a lower alkoxycarbonyl group can be removed, for example, by alkaline hydrolysis.

The reaction of a compound of formula II with a compound of formula III in accordance with process embodiment (a) can be carried out in the absence of a solvent. If, however, the reaction is carried out in the presence of a solvent, the solvent is conveniently an organic solvent such as an aromatic hydrocarbon, for example, benzene or toluene, a lower alkanol, for example, methanol or ethanol, a chlorinated hydrocarbon, for example, methylene chloride, trichloroethylene, chloroform, carbon tetrachloride or chlorobenzene, an aliphatic or cyclic ether, for example, diethyl ether, tetrahydrofuran or dioxane, dimethylformamide or dimethylsulfoxide. The reaction is conveniently carried out at a temperature in the range of from about 30° C. to about 200° C., preferably at a temperature in the range of from about 60° C. to about 150° C. The reaction is advantageously carried out in the presence of an acid-binding agent, for example, in the presence of an alkali carbonate, such as potassium carbonate, or in the presence of an excess of the starting material of formula III.

The enamine starting materials of formula IV can be prepared by reacting a corresponding 10-oxo compound with a compound of formula III. This reaction can be carried out, for example, in the presence of a strong acidic agent in an aromatic solvent with heating, for example, at a temperature in the range of from about 80° C. to about 150° C. Examples of acidic agents which can be used are mineral acids such as methanesulfonic acid, p-toluenesulfonic acid, or the like. The preferred aromatic solvents are benzene, toluene, and o-, m- or p-xylene. During the heating there is formed an azeotrope between the solvent and the water formed in the reaction, which can be removed by distillation. The water formed can also be removed by the addition of a dehydrating agent such as titanium tetrachloride.

An obtained enamine alcohol of formula IV, that is, a compound of formula IV wherein R is hydroxy, can be converted into the corresponding ester of formula IV, preferably by reaction with the corresponding alkanecarboxylic acid in the presence of a non-acidic dehydrating agent, for example, dicyclohexylcarbodiimide, carbonyldiimidazole, or the like.

The reduction of an enamine of formula IV in accordance with process embodiment (b) is preferably carried out by treatment with an alkali metal borohydride in the presence of a strong acid. Sodium borohydride or potassium borohydride, particularly sodium borohydride, is preferably used as the alkali metal borohydride. However, lithium borohydride can also be used. The strong acid can be either an organic acid or an inorganic acid. Suitable organic acids comprise straight-chain or branched-chain, lower mono- or dicarboxylic acids which contain up to 4 carbon atoms and which may be halogen-substituted, for example, formic acid, acetic acid, trichloroacetic acid, trifluoroacetic acid, propionic acid, isobutyric acid, oxalic acid and the like. Acetic acid and oxalic acid are preferred. Suitable inorganic acids comprise, in particular, sulfuric acid, hydrohalic acids, especially hydrochloric acid, and the like. A preferred inorganic acid is concentrated sulfuric acid. Since the enamines of formula IV are unstable in the presence of water, the reduction is conveniently carried out in the absence of water. Therefore, preferably only anhydrous acids or only those acids which, if they contain some water, do not release water, for example, concentrated sulfuric acid, are used. The reduction with an alkali metal borohydride and a strong acid is advantageously carried out in an ether such as diethyl ether, tetrahydrofuran, dioxane, diethyleneglycol dimethyl ether (diglyme) or dimethoxyethane, at a temperature in the range of from about room temperature and the reflux temperature of the mixture. The reduction is preferably carried out under reflux conditions. The reduction of an enamine of formula IV can also be carried out by other methods, for example, by treatment with formic acid or zinc and glacial acetic acid. The latter reductions are also preferably carried out at a temperature in the range of from about room temperature to the reflux temperature of the mixture, preferably at the reflux temperature.

The starting materials of formula V can be prepared, for example, by reacting a compound of formula II with a mono-N-protected piperazine such as N-carbethoxypiperazine. The reaction product is subsequently subjected to an alkaline saponification, for example, using aqueous alkali.

The compounds yielding the group R which are reacted with the starting materials of formula V can be, for example, the compounds of formula IX. On the other hand, there may also be used the corresponding alkenes yielding the group R which, with the uptake of a hydrogen atom and saturation of a double bond, can be reacted with a starting material of formula V to give the desired compound of formula I. Other compounds yielding the group R are the corresponding cyclic ethers, these lead to compounds of formula I wherein R is hydroxyalkyl. Examples of such cyclic ethers are oxirane, methyloxirane, oxetane and tetrahydrofuran.

Compounds of formula IX wherein R is a group of formula (a), namely compounds of the formula

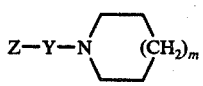

XI wherein X, Y, Z and m are as earlier described, can be obtained, for example, by converting a lactam of the formula

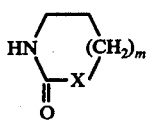   XII wherein X and m are as earlier described,
into a corresponding alkali metal salt, for example, the sodium salt. This conversion can be carried out, for instance, by treating a lactam of formula XII with an alkali metal, an alkali metal hydride or an alkali metal amide in an aromatic hydrocarbon, for example, benzene or toluene, or dimethylformamide. The resulting alkali metal salt is subsequently reacted with a compound of the formula $R_7O—Y—Hal$   XIII wherein Y is as earlier described, Hal is halogen and $R_7$ is a suitable protecting group, for example, benzyl or 2-tetrahydropyranyl.

The protecting group denoted by $R_7$ in the reaction product is then cleaved hydrogenolytically, when $R_7$ is benzyl, or hydrolytically, when $R_7$ is 2-tetrahydropyranyl. The resulting hydroxy compound is treated with a halogenating agent, for example, thionyl chloride, or with an alkyl-substituted or aryl-substituted sulfonic acid halide, for example, the chloride, to give a starting material of formula XI.

The alkenes corresponding to the compounds of formula XI are obtained by replacing the compounds of formula XIII with a corresponding alkene of the formula Y'—Hal   XIV wherein Hal is as previously described and Y' is an olefinic group containing one hydrogen atom less then Y as earlier described.

An alkanoyl ester yielding the group R which may be used in process embodiment (c) can be prepared from a corresponding hydroxy-lower alkyl, hydroxy-lower alkenyl alkyl or hydroxy-lower alkynyl alkyl compound by reaction with a corresponding alkanecarboxylic acid halide.

The reaction of a starting material of formula V with a compound yielding the group R in accordance with process embodiment (c) is conveniently carried out in an inert organic solvent, for example, an aromatic hydrocarbon such as benzene or toluene, a chlorinated hydrocarbon such as chloroform, an ether such as dioxane or dimethoxyethane, a lower alkanol such as methanol, ethanol or butanol, a ketone such as acetone or methyl ethyl ketone, dimethylformamide or dimethylsulfoxide. The reaction is preferably carried out at a temperature in the range of from about room temperature and the boiling point of the reaction mixture. When a compound of formula IX is used, the reaction is preferably carried out in the presence of an acid-binding agent; for example, in the presence of an alkali metal carbonate such as sodium carbonate or potassium carbonate, or in the presence of an inert organic base such as triethylamine. An excess of the base of formula V can also be used as the acid-binding agent.

The esterification of a starting material of formula VI in accordance with process embodiment (d) is conveniently carried out by treatment at room temperature to about 150° C, e.g. by heating to a temperature in the range of from about 50° to about 150° C, with a reactive derivative of the appropriate alkanecarboxylic acid, for example, the acid chloride or acid anhydride. The esterification can also be carried out by reaction with an alkanecarboxylic acid in the presence of a strong acidic catalyst such as sulfuric acid or p-toluenesulfonic acid, or in the presence of a dehydrating agent such as dicyclohexylcarbodiimide or carbonyldiimidazole. The esterification is preferably carried out in an organic solvent, for example, benzene, toluene or pyridine.

The starting materials of formula VII can be prepared, for example, by reacting a compound of formula II with a piperazine derivative of the formula

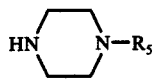   XV wherein $R_5$ is lower alkanoyl, hydroxy-lower alkanoyl or lower alkoxycarbonyl.

The lower alkanoyl denoted by $R_5$ in formulas XV and VII is straight-chain or branched-chain group derived from alkanecarboxylic acid containing at least two carbon atoms, preferably with a maximum of 6 carbon atoms, such as acetyl, propionyl, isobutyryl or n-hexanoyl. The hydroxy-lower alkanoyl groups have an analogous significance. The lower alkoxycarbonyl denoted by $R_5$ preferably contains 2 to 6, most preferably 2 to 4 carbon atoms such as methoxycarbonyl, ethoxycarbonyl or isopropoxycarbonyl.

The preparation of the starting materials of formula VII from the compounds of formulas II and XV is carried out in essentially the same manner and under the same conditions as described hereinbefore for the reaction of a compound of formula II with a compound of formula III.

The reduction of a starting material of formula VII in accordance with process embodiment (e) is preferably carried out using a complex aluminum hydride, for example, an alkali metal aluminum hydride such as lithium aluminum hydride, sodium aluminum hydride or potassium aluminum hydride or, preferably, an alkali metal dihydro-bis(2-methoxyethoxy)-aluminate such as sodium dihydro-bis(2-methoxyethoxy)-aluminate. The reduction is preferably carried out in an inert organic solvent, for example, benzene, tetrahydrofuran or diethyl ether. The temperature at which this reduction is carried out is not critical, but the reduction is conveniently carried out at a temperature in the range of from about room temperature to the boiling point of the mixture.

When it is desired to prepare a compound of formula I wherein $R_1$–$R_4$ is hydroxy, there is preferably used a starting material of formula II, IV, V, VI or VII in which the corresponding hydroxy group is protected, for example, by a lower alkyl or benzyl group. After carrying out the respective embodiment of the process using such a starting material, the protecting group is cleaved, preferably by treatment with a boron trihalide, for example, boron tribromide or boron trichloride, in an anhydrous inert solvent, for example, benzene, toluene or xylene, or a halogenated hydrocarbon such as methylene chloride, chloroform or carbon tetrachloride. The cleavage of the protecting group is preferably carried out at a low temperature, for example, at a temperature in the range of from about −70° C. to room temperature.

The bases of formula I form acid addition salts with pharmaceutically acceptable inorganic acids, for example, with hydrohalic acids such as hydrochloric acid, hydrobromic acid or hydroiodic acid, or with other mineral acids such as sulfuric acid, phosphoric acid, nitric acid, or the like, and with organic acids, for example, tartaric acid, citric acid, camphor-sulfonic acid, methanesulfonic acid, toluenesulfonic acid, salicyclic acid, ascorbic acid, maleic acid, mandelic acid or the like. The preferred salts are the hydrohalides, especially the hydrochlorides, the maleates and the methanesulfonates. The pharmaceutically acceptable acid addition salts are preferably prepared in a suitable solvent, for example, ethanol, acetone or acetonitrile, by treating the free base with an appropriate nonaqueous acid. Depending on the molar ratio of the free base to acid, there is obtained, because of the two nitrogen atoms on the piperazine group, a salt containing one or two mols of acid per mol of base, that is, a mono or di salt. In the working-up of a di salt that is obtained, the corresponding di or mono salt is obtained depending on the solubility of the mono or di salt in the solvent used.

The bases of formula I are partly crystalline, solid substances which have a relatively good solubility in dimethylsulfoxide, dimethylformamide, chlorinated hydrocarbons such as chloroform or methylene chloride, aromatic hydrocarbons such as benzene or toluene, and in alkanols such as methanol or ethanol and which are relatively insoluble in water.

The pharmaceutically acceptable acid addition salts of the bases of formula I are crystalline, solid substances. They have a relatively good solubility in dimethylsulfoxide, dimethylformamide or alkanols such as methanol or ethanol. The salts are also partially soluble in chloroform, methylene chloride or water, and relatively insoluble in benzene, ether or petroleum ether.

In order to demonstrate the advantageous pharmacological activity of the dibenz[b,f]oxepin derivatives of formula I of the invention, the following representative derivatives, test compounds, were tested:

Derivative A: 1-[10,11-Dihydro-2,8-dimethyl-dibenz[b,f]oxepin-10-yl]-4-methyl-piperazine dihydrochloride.

Derivative B: 3-{4-[2-Chloro-10,11-dihydro-dibenz[b,f]oxepin-10-yl]-1-piperazinyl}-1-propanol dihydrochloride.

Derivative C: 3-[2-{4-[2,8-Dichloro-10,11-dihydro-dibenz[b,f]oxepin-10-yl]-1-piperazinyl}-ethyl]-2-oxazolidinone dihydrochloride.

Derivative D: 3-[2-{4-[10,11-Dihydro-2,8-dimethyl-dibenz[b,f]oxepin-10-yl]-1-piperazinyl}-ethyl]-2-oxazolidinone dihydrochloride.

Derivative E: 3-[2-{4-[2-Chloro-8-fluoro-10,11-dihydro-dibenz[b,f]oxepin-10-yl]-1-piperazinyl}-ethyl]-2-oxazolidinone maleate.

Derivative F: 3-[2-{4-[8-Fluoro-10,11-dihydro-2-methyl-dibenz[b,f]oxepin-10-yl]-1-piperazinyl}-ethyl]-2-oxazolidinone dihydrochloride.

Derivative G: 3-[2-{4-[2-Chloro-10,11-dihydro-dibenz[b,f]oxepin-10-yl]-1-piperazinyl}-ethyl]-2-oxazolidinone maleate.

Derivative H: 3-{4-[2-Chloro-10,11-dihydro-dibenz[b,f]oxepin-10-yl]-1-piperazinyl}-propionic acid nitrile.

Chlorpromazine, a recognized central depressant or neuroleptic agent was used as the standard.

The central depressant or neuroleptic properties of the test substance were determined numerically by way of the following two tests: (I) determination of homovanillic acid and (II) the "Pole Climbing" test.

I. Determination of Homovanillic Acid

Rats are injected with the derivative to be tested two hours before they are killed. Homovanillic acid is extracted from the supernatant of the brain homogenate into butyl acetate and later into an aqueous solution, and oxidized with potassium ferricyanide to a fluorescent dimer. From the increased concentration of homovanillic acid (HVA) it can be concluded that the derivative under investigation acts like chlorpromazine, i.e., it increases the turnover of dopamine in the basic ganglia. The homovanillic acid titre in untreated rats is arbitrarily fixed at 100%.

RESULTS:
| Derivative | Dose mg/kg. p.o. | Increase in HVA, % |
|---|---|---|
| A | 2 | 235 |
| B | 3.5 | 260 |
| C | 5 | 365 |
| D | 15 | 335 |
| E | 10 | 260 |
| F | 50 | 265 |
| G | 50 | 225 |
| H | 50 | 275 |
| Chlorpromazine | 20 | 320 |

In this test, derivatives A–E show an activity which, on a dose basis, exceeds that of chlorpromazine, while the activity of derivatives F–H almost approaches that of chlorpromazine.

II. "Pole Climbing" Test

This test provides information about behavior reactions of rats. Rats are trained to avoid, by climbing up a vertical pole in the test chamber, an electrical impulse—unconditioned impulse—released via the wire-latticed floor some seconds after an acoustic signal—conditioned impulse.

The blocking of the conditioned reaction is designated by the parameter $ED_{50}$ (mg/kg. p.o.) and the blocking of the unconditioned reaction is designated by the parameter $ED_{10}$ (mg/kg. p.o.).

The parameter $ED_{50}$—blocking of the conditioned reaction—provides a measure of the strength of the neuroleptic activity of the derivative under investigation. The quotient $ED_{10}$—blocking of the unconditioned reaction—$ED_{50}$—blocking of the conditioned reaction—provides a measure of the quality of activity of the derivative under investigation since, when the quotient increases, a greater selectivity of the neuroleptic activity, that is, slighter neurotoxic side-effects, is present.

RESULTS:
| Derivative | $ED_{50}$ (blocking of the conditioned reaction)mg/kg.p.o. | Quotient $ED_{10}$ (blocking of the unconditioned reaction)/ $ED_{50}$ (blocking of the conditioned reaction) |
|---|---|---|
| A | 3.2 | 3.1 |
| D | 7.6 | 5.6 |
| E | 3.5 | 2.8 |
| F | 7.0 | 5.1 |
| G | 15.5 | 3.5 |
| H | 14.0 | >21 |
| Chlor- | | |

-continued

RESULTS:

| Derivative | $ED_{50}$ (blocking of the conditioned reaction) mg/kg.p.o. | Quotient $ED_{10}$ (blocking of the unconditioned reaction)/ $ED_{50}$ (blocking of the conditioned reaction) |
|---|---|---|
| promazine | 11.8 | 2.5 |

In this test, derivatives A–F exhibit a neuroleptic strength of action which exceeds that of chlorpromazine, while the strength of action of derivatives G and H is somewhat lower than that of chlorpromazine. The quality (selectivity) of the neuroleptic activity is, however, superior in all of derivatives A–H to that of chlorpromazine; in the case of derivative H this superiority is particularly evident.

In order to demonstrate the lack of any significant cataleptic side-effects, the following test was carried out:

III. Catalepsy Test

A cataleptic activity—"wax rigidity", i.e., abnormally long retention of a fixed body position—in central depressant or neuroleptically active compounds is considered to be an undesirable side-effect and is produced by motor disorders. Representative dibenz[b,f]oxepin derivatives provided by this invention were administered intraperitoneally to rats. The animals are considered to be cataleptic when the homolateral extremities remain in a crossed position for at least 10 seconds. The number of cataleptic animals is noted every 30 minutes for 6 hours. The $ED_{50}$ is the dose at which 50% of the animals show catalepsy.

RESULTS:

| Derivative | $ED_{50}$ mg/kg. |
|---|---|
| D | 14 |
| F | 30 |
| G | 50 |
| H | >30 |
| Chlorpromazine | 6 |

From the foregoing Table, it will be noted that derivatives D, F and G possess only about one half to about one eighth of the undesired cataleptic side effect of chlorpromazine and that derivative H possesses less than one fifth of the undesired cataleptic side-effect of chlorpromazine.

IV. Toxicity

The following values for acute toxicity in the mouse show that the tested derivatives are significantly less toxic than chlorpromazine. The figures relate to a duration of activity over a period of 24 hours:

| Derivative | $LD_{50}$ mg/kg. p.o. |
|---|---|
| A | 900 |
| B | 375 |
| C | 900 |
| D | 750 |
| E | 900 |
| F | 450 |
| G | 450 |
| H | 1500 |
| Chlorpromazine | 200 |

The dibenz[b,f]oxepin derivatives provided by the present invention can be used as medicaments, for example, in the form of pharmaceutical preparations which contain them in association with a compatible pharmaceutical carrier. Such a carrier can be an organic or inorganic inert carrier material suitable for enteral, for example, oral, or parenteral administration, for example, water, gelatin, lactose, starch, magnesium stearate, talc, vegetable oils, gum arabic, polyalkyleneglycols or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants such as preserving, stabilizing, wetting or emulsifying agents, salts for varying the osmotic pressure or buffers. They may also contain other therapeutically valuable substances.

Pharmaceutical dosage forms can contain about 1 mg. to 200 mg. of a compound of formula I or of its pharmaceutically acceptable acid addition salt. Oral dosages can comprise from about 0.1 mg/kg. per day to about 7.5 mg/kg. per day. Parenteral dosages can comprise from about 0.01 mg/kg. per day to about 0.75 mg/kg. per day. However, the foregoing ranges can be varied upwards or downwards according to the individual requirements.

The following Examples further illustrate the invention. All temperatures are in degrees Centigrade, unless otherwise specified.

EXAMPLE 1

Preparation of 3-[2-{4-[10,11-dihydro-2,8-dimethyl-dibenz[b,f]oxepin-10-yl]-1-piperazinyl}-ethyl]-2-oxazolidinone 14.5 G. of 1-[10,11-dihydro-2,8-dimethyl-dibenz[b,f]oxepin-10-yl]-piperazine are stirred at reflux for 3 hours together with 13.4 g. of 3-(2-chloroethyl)-2-oxazolidinone, 4.9 g. of sodium carbonate and 0.6 g. of sodium iodide in 80 ml. of n-butanol. Then, the solvent is evaporated under vacuo and the residue is partitioned between water and chloroform. The aqueous phase is extracted two additional times with chloroform. The chloroform solutions are washed with water and with sodium chloride solution, dried over sodium sulfate and evaporated. The residue is taken up in a small amount of ether, whereby 3-[2-{4-[10,11-dihydro-2,8-dimethyl-dibenz[b,f]oxepin-10-yl]-1-piperazinyl}-ethyl]-2-oxazolidinone, having a melting point of 175°–176° crystallizes out. The dihydrochloride (crystallized from ethanol/ether) melts at 183° (with decomposition).

The 1-[10,11-dihydro-2,8-dimethyl-dibenz[b,f]oxepin-10-yl]-piperazine used as the starting material can be prepared as follows:

20 G. of 5-methyl-anthranilic acid are suspended in 200 ml. of 3-N hydrochloric acid at 0° C. A solution of 10 g. of sodium nitrite and 20 ml. of water is added dropwise thereto with stirring and the mixture is further stirred for 25 minutes at 0° C. A solution of 26.5 g. of potassium iodide, 30 ml. of 3-N hydrochloric acid and 30 ml. of water is then added dropwise at 5°–10° C. The mixture is stirred for an additional 30 minutes at room temperature and for 2 hours at reflux. The mixture is cooled and sodium thiosulfate is added until the solution is yellow (5 g.). The crystalline 2-iodo-5-methyl-benzoic acid obtained is removed by filtration under vacuum and washed neutral with water. The crude acid is dissolved in ether, washed well with sodium thiosulfate solution and water, dried over sodium sulfate and evaporated, and there are obtained light-brown crystals having a melting point of 100°–112° C.

393 G. of 2-iodo-5-methyl-benzoic acid in 150 ml. of nitrobenzene are heated to 145° C. 138 G. of potassium carbonate are added thereto in small portions with stirring. Subsequently, 156 ml. of 4-methyl-phenol and 276 g. of potassium carbonate are added. To the resulting mixture, 3 g. of copper powder are carefully added, and the mixture is subsequently stirred at 165° C. for 20 minutes. After cooling, 1.25 liters of water are added to the mixture which is then extracted twice with ether. The aqueous phase is acidified with hydrochloric acid and extracted twice with ether. The ethereal solutions are washed with water, dried over sodium sulfate and concentrated in vacuo. The residue (brown crystals) is recrystallized from 1100 ml. of methanol and 700 ml. of water, and there is obtained 2-(4-methylphenoxy)-5-methyl-benzoic acid, which after repeated recrystallization from methanol/water, melts at 113°–115° C.

A solution of 121 g. of 2-(4-methyl-phenoxy)-5-methyl-benzoic acid in 600 ml. of tetrahydrofuran is slowly added dropwise, with cooling in an icebath, to 420 ml. of a 70% solution of sodium dihydro-bis(1-methoxyethoxy)aluminate in benzene and stirred for an additional hour at room temperature. To the obtained clear solution, 800 ml. of 20% aqueous sodium hydroxide solution are carefully added dropwise. Then, the organic phase is separated. The aqueous phase is extracted three additional times with ether. The organic extracts are washed with saturated sodium chloride solution and the latter dried over sodium sulfate. After evaporation of the ether, there is obtained 2-(4-methyl-phenoxy)-5-methyl-benzyl alcohol as an oil.

36.5 Ml. of thionyl chloride are added dropwise at 10°–15° C. with stirring and cooling with ice to a solution of 110 g. of 2-(4-methyl-phenoxy)-5-methyl-benzyl alcohol in 78 ml. of pyridine. The mixture is stirred for an additional 1 hour at 10° C. and then diluted with 200 ml. of benzene. Then, 200 ml. of water are carefully added dropwise with ice-cooling. The aqueous phase is separated and the organic phase washed successively with dilute hydrochloric acid, water and saturated sodium bicarbonate solution. The aqueous phases are each extracted once more with benzene. The combined benzene extracts are dried over sodium sulfate and evaporated to dryness in vacuo and there is obtained 3-chloromethyl-4-(4-methyl-phenoxy)-toluene as an oil.

A solution of 108 g. of 3-chloromethyl-4-(4-methyl-phenoxy)-toluene in 70 ml. of dimethylsulfoxide is added dropwise at 20°–25° C. to a suspension of 23 g. of sodium cyanide in 35 ml. of dimethylsulfoxide. The mixture is subsequently stirred for 4 hours at 36° C., then diluted with 1 liter of water and extracted three times with benzene. The benzene extracts are washed three times with water, then dried over sodium sulfate and evaporated in vacuo, and there is obtained crude 2-(4-methyl-phenoxy)-5-methyl-phenylacetonitrile as a brown oil.

A solution of 95 g. of crude 2-(4-methyl-phenoxy)-5-methyl-phenylacetonitrile in 500 ml. of ethanol is treated with a solution of 67 g. of potassium hydroxide in 120 ml. of water and heated to reflux for 5 hours. Then, the ethanol is evaporated in vacuo and the residue diluted with 500 ml. of water. The resulting mixture is extracted twice with ether. The ethereal extracts are extracted twice with sodium bicarbonate solution. The combined aqueous solutions are acidified and extracted three times with ether. The ethereal extracts are washed with saturated sodium chloride solution, dried over sodium sulfate and evaporated in vacuo, and there is obtained 2-(4-methyl-phenoxy)-5-methyl-phenylacetic acid which, after recrystallization from methanol/water, melts at 101°–104° C.

200 G. of polyphosphoric acid are mixed with 49.5 g. of 2-(4-methyl-phenoxy)-5-methyl-phenylacetic acid at 100° C. and stirred at this temperature for 45 minutes. The mixture is cooled, ice is added and the mixture is extracted three times with ether. The ethereal extracts are washed successively with water, saturated sodium bicarbonate solution and saturated sodium chloride solution, dried over sodium sulfate and evaporated to dryness in vacuo. The residue is distilled (boiling point 140° C/0.1 Torr), and there is obtained 10,11-dihydro-2,8-dimethyl-dibenz[b,f]oxepin-10-one which crystallizes from methanol; melting point 62°–62.5° C.

A solution of 11.35 ml. of titanium (IV) chloride in 135 ml. of benzene is added dropwise with stirring and cooling at 20°–25° C. to a solution of 30 g. of 10,11-dihydro-2,8-dimethyl-dibenz[b,f]oxepin-10-one and 80 ml. of N-ethoxycarbonylpiperazine in 300 ml. of benzene. Then, the mixture is stirred for 4 hours at reflux and cooled. The cooled mixture is poured into a solution of 12 g. of sodium bicarbonate in 300 ml. of water. The precipitated titanium dioxide is removed by filtration and washed well with benzene. The filtrate is washed four additional times with water. The aqueous phases are extracted again with benzene. The combined benzene extracts are dried over sodium sulfate and evaporated in vacuo, and there is obtained 4-[2,8-dimethyl-dibenz[b,f]oxepin-10-yl]-1-piperazinecarboxylic acid ethyl ester as an oil.

48.6 G. of 4-[2,8-dimethyl-dibenz[b,f]oxepin-10-yl]-1-piperazinecarboxylic acid ethyl ester are dissolved in 750 ml. of glacial acetic acid. 18.9 G. of sodium borohydride are added in small portions within 20 minutes with stirring and cooling in such a manner that the temperature does not exceed 25° C. The mixture is stirred for an additional 30 minutes at 25° C. and then the glacial acetic acid is removed by distillation in vacuo. The residue is partitioned between chloroform and aqueous sodium hydroxide solution. The organic phase is separated and washed with water. The aqueous phases are extracted two additional times with chloroform. The combined chloroform extracts are dried over sodium sulfate, evaporated in vacuo, and there is obtained crude 4-[10,11-dihydro-2,8-dimethyl-dibenz[b,f]oxepin-10-yl]-1-piperazinecarboxylic acid ethyl ester as an oil.

22.0 G. of 4-[10,11-dihydro-2,8-dimethyl-dibenz[b,f]oxepin-10-yl]-1-piperazinecarboxylic acid ethyl ester and 22 g. of potassium hydroxide are stirred in 320 ml. of ethyleneglycol and 1.5 ml. of water for 90 minutes at 160° C. After cooling, the mixture is diluted with 1.3 liters of water and extracted three times with ether. The ethereal extracts are washed twice with saturated sodium chloride solution, dried over sodium sulfate, evaporated in vacuo, and there is obtained crude 1-[10,11-dihydro-2,8-dimethyl-dibenz[b,f]oxepin-10-yl]-piperazine as an oil.

EXAMPLE 2

Preparation of 3-[2-{4-[8-fluoro-10,11-dihydro-2-methyl-dibenz[b,f]oxepin-10-yl]-1-piperazino}-ethyl]-2-oxazolidinone 18 G. of 1-[8-fluoro-10,11-dihydro-2-methyl-dibenz[b,f]oxepin-10-yl]piperazine are stirred at reflux for 3 hours together with 17.2 g. of 3-(2-chloroethyl)-2-oxazolidinone, 6.0 g. of sodium carbonate and 0.8 g. of sodium iodide in 100 ml. of butanol. Then, the solvent is evaporated under reduced pressure and the residue partitioned between water and chloroform. The organic phase is washed with water, dried over sodium sulfate and evaporated under reduced pressure. The residue is crystallized by the addition of ether, removed by filtration, and there is obtained 3-[2-{4-[8-fluoro-10,11-dihydro-2-methyl-dibenz[b,f]oxepin-10-yl]-1-piperazino}-ethyl]-2-oxazolidinone having a melting point of 145°–147° C. after recrystallization from ethanol. The monohydrochloride melts at 229°–230° C. (with decomposition).

The 1-[8-fluoro-10,11-dihydro-2-methyl-dibenz[b,f]oxepin-10-yl]piperazine (an oil) used as the starting material is prepared from 2-iodo-5-methyl-benzoic acid and 4-fluoro-phenol in a manner analogous to that described in Example 1, via the following intermediates:

2-(4-fluoro-phenoxy)-5-methyl-benzoic acid having a melting point of 127°–128° C.;

2-(4-fluoro-phenoxy)-5-methyl-benzyl alcohol (liquid; boiling point 140°–145° C/0.15 Torr);

3-chloromethyl-4-(4-fluoro-phenoxy)-toluene (oil);

2-(4-fluoro-phenoxy)-5-methyl-phenylacetonitrile (oil);

2-(4-fluoro-phenoxy)-5-methyl-phenylacetic acid having a melting point of 116°–119° C.;

8-fluoro-10,11-dihydro-2-methyl-dibenz[b,f]oxepin-10-one, having a melting point of 75°–76° C.;

4-[8-fluoro-2-methyl-dibenz[b,f]oxepin-10-yl]-1-piperazinecarboxylic acid ethyl ester, having a melting point of 106°–108.5° C.;

4-[8-fluoro-10,11-dihydro-2-methyl-dibenz[b,f]oxepin-10-yl]-1-piperazinecarboxylic acid ethyl ester having a melting point of 92°–96° C.

EXAMPLE 3

Preparation of 3-[2-{4-[2-chloro-8-fluoro-10,11-dihydro-dibenz[b,f]oxepin-10-yl]-1-piperazinyl}-ethyl]-2-oxazolidinone 1-[2-chloro-8-fluoro-10,11-dihydro-dibenz[b,f]oxepin-10-yl]-piperazine is reacted with 3-(2-chloro-ethyl)-2-oxazolidinone in the manner described in Example 1, and there is obtained 3-[2-{4-[2-chloro-8-fluoro-10,11-dihydro-dibenz[b,f]oxepin-10-yl]-1-piperazinyl}-ethyl]-2-oxazolidinone as an oil. The maleate, prepared in acetone, melts at 180°–182° C.

The 1-[2-chloro-8-fluoro-10,11-dihydro-dibenz[b,f]oxepin-10-yl]piperazine used as the starting material can be prepared as follows:

448 G. of 4-fluoro-phenol and 742 g. of 2-chloro-5-nitro-benzaldehyde are added to a solution of 184 g. of sodium hydroxide in 7.4 liters of water. The mixture is then left to cool to room temperature. The precipitate is removed by filtration, washed carefully with water, and there is obtained 2-(4-fluoro-phenoxy)-5-nitro-benzaldehyde, having a melting point of 125°–126° C.

183.4 G. of 2-(4-fluoro-phenoxy)-5-nitro-benzaldehyde are stirred at reflux for 20 minutes together with 71 g. of potassium bicarbonate and 82 g. of acetylglycine in 395 ml. of acetic anhydride. Then, there are added successively 1.62 liters of glacial acetic acid, 870 ml. of water and 675 ml. of concentrated hydrochloric acid, and the mixture is stirred for 5 hours at reflux. The resulting mixture is cooled and 1.2 liters of water are added. The mixture is extracted with 3.1 liters of methylene chloride in 3 portions. The methylene chloride solutions are washed twice with 2 liters of water each time and subsequently extracted with a solution of 250 g. of sodium carbonate in 4.5 liters of water. The obtained bicarbonate solutions are acidified with hydrochloric acid and extracted with ethyl acetate. The ethyl acetate solutions are dried over sodium sulfate and evaporated in vacuo. The crystalline residue is boiled out with 400 ml. of benzene. The crystals are removed by filtration and there is obtained 2-(4-fluoro-phenoxy)-5-nitro-phenylpyruvic acid having a melting point of 142°–143° C. By concentration of the filtrate, there is obtained an additional amount of this compound.

560 Ml. of a 10% aqueous solution of hydrogen peroxide are added dropwise at 0° over a period of 75 minutes to a solution of 142 g. of 2-(4-fluoro-phenoxy)-5-nitro-phenylpyruvic acid in 2.23 liters of 10% sodium hydroxide solution cooled to 0° C. The mixture is subsequently stirred for 3 hours at 25° C. and then acidified with 500 ml. of concentrated hydrochloric acid with cooling. This mixture is extracted twice with methylene chloride. The methylene chloride solutions are washed with water, dried over sodium sulfate and concentrated in vacuo. The residue is crystallized from benzene/hexane, and there is obtained 2-(4-fluoro-phenoxy)-5-nitro-phenylacetic acid having a melting point of 129°–130° C.

125 G. of 2-(4-fluoro-phenoxy)-5-nitro-phenylacetic acid are stirred in 586 g. of polyphosphoric acid for 2 hours at 100° C. Then, the mixture is treated with ice and extracted with 6 liters of ethyl acetate. In so doing, a portion of the resulting 8-fluoro-10,11-dihydro-2-nitro-dibenz[b,f]oxepin-10-one remains undissolved and is removed by filtration. The ethyl acetate solution is washed with water, sodium bicarbonate solution and water, dried over sodium sulfate, concentrated and 8-fluoro-10,11-dihydro-2-nitro-dibenz[b,f]oxepin-10-one, having a melting point of 159°–160° C. crystallizes out.

95 G. of 8-fluoro-10,11-dihydro-2-nitro-dibenz[b,f]oxepin-10-one in 1300 ml. of ethanol and 2000 ml. of ethyl acetate are hydrogenated in the presence of 0.65 g. of platinum dioxide. The solution is filtered clear. Upon concentration, 2-amino-8-fluoro-10,11-dihydro-dibenz[b,f]oxepin-10-one crystallizes out; melting point 161°–162° C. (after recrystallization from benzene/hexane).

A solution of 3.6 g. of sodium nitrite in 12 ml. of water is added dropwise at 0°–5° C. over a period of 5 minutes to a solution of 10 g. of 2-amino-8-fluoro-10,11-dihydro-dibenz[b,f]oxepin-2-one in 73 ml. of 2-N aqueous methanesulfonic acid solution cooled to 0° C. The mixture is subsequently stirred for an additional 5 minutes at 0°–5° C. The resulting diazonium salt solution is poured into a mixture of 170 ml. of ethyl acetate at about 20° C. and a solution of 13.0 g. of copper (I) chloride in 155 ml. of concentrated hydrochloric acid, and the resulting mixture is stirred at this temperature for an additional 10 minutes. The phases are separated and the ethyl acetate solution is washed several times with saturated sodium chloride solution. Then, the ethyl acetate phase is dried over sodium sulfate and evaporated in vacuo. The residue is dissolved in benzene and filtered through 31 g. of silica gel. The benzene eluates are evaporated in vacuo, the residue crystallized from isopropanol, and there is obtained 2-chloro-8-fluoro-10,11-dihydro-dibenz[b,f]oxepin-10-one, having a melting point of 91°–92° C.

2-Chloro-8-fluoro-10,11-dihydro-dibenz[b,f]oxepin-10-one is converted into the desired 1-[2-chloro-8- fluoro-10,11-dihydro-dibenz[b,f]oxepin-10-yl]piperazine (an oil) in the same manner as described in Example 1, via the following intermediates:

4-[2-chloro-8-fluoro-dibenz[b,f]oxepin-10-yl]-piperazinecarboxylic acid ethyl ester having a melting point of 129°–130° C;

4-[2-chloro-8-fluoro-10,11-dihydro-dibenz[b,f]oxepin-10-yl]-piperazinecarboxylic acid ethyl ester having a melting point of 115°–116° C.

EXAMPLE 4

Preparation of
3-[2-{4-[2,8-dichloro-10,11-dihydro-dibenz[b,f]oxepin-10-yl]-1-piperazinyl}-ethyl]-2-oxazolidinone dihydrochloride 1-[2,8-dichloro-10,11-dihydro-dibenz[b,f]oxepin-10-yl]-piperazine is reacted with 3-(2-chloro-ethyl)-2-oxazolidinone in the manner described in Example 1, and there is obtained 3-[2-{4-[2,8-dichloro-10,11-dihydro-dibenz[b,f]oxepin-10-yl]-1-piperazinyl}-ethyl]-2-oxazolidinone dihydrochloride having a melting point of 187°–188° C (with decomposition).

The 1-[2,8-dichloro-10,11-dihydro-dibenz[b,f]oxepin-10-yl]-piperazine (melting point 120°–122° C.) used as the starting material can be prepared from 5-chloro-2-iodo-benzoic acid and 4-chloro-phenol in the manner described in Example 1, via the following intermediates:

2-(4-chloro-phenoxy)-5-chloro-benzoic acid having a melting point of 132°–134° C;

2-(4-chloro-phenoxy)-5-chloro-benzyl alcohol (oil);

1-chloro-3-chloromethyl-4-(4-chloro-phenoxy)-benzene (oil);

2-(4-chloro-phenoxy)-5-chloro-phenylacetonitrile (oil);

2-(4-chloro-phenoxy)-5-chloro-phenylacetic acid having a melting point of 113°–115° C;

2,8-dichloro-10,11-dihydro-dibenz[b,f]oxepin-10-one having a melting point of 118°–119° C;

4-[2,8-dichloro-dibenz[b,f]oxepin-10-yl]-1-piperazinecarboxylic acid ethyl ester having a melting point of 130°–132° C;

4-[2,8-dichloro-10,11-dihydro-dibenz[b,f]oxepin-10-yl]-1-piperazinecarboxylic acid ethyl ester having a melting point of 129°–131° C

EXAMPLE 5

Preparation of
3-[3-{4-[10,11-dihydro-3-methoxy-8-methyl-dibenz[b,f]oxepin-10-yl]-1-piperazinyl}-propyl]-2-oxazolidinone 8.1 G. of 1-[10,11-dihydro-3-methoxy-8-methyl-dibenz[b,f]oxepin-10-yl]piperazine are stirred at reflux for 18 hours together with 5.25 g. of 3-(3-chloropropyl)-2-oxazolidinone, 2.7 g. of sodium carbonate and 0.4 g. of sodium iodide in 40 ml. of butanol. Then, the solvent is evaporated under reduced pressure, and the residue partitioned between chloroform and water. The aqueous phase is separated and extracted two additional times with chloroform. The chloroform solutions are washed with aqueous sodium chloride solution, dried over sodium sulfate and evaporated under reduced pressure. The residue is dissolved in benzene and chromatographed over 200 g. of silica gel. Impurities are first eluted with benzene. Then, using benzene/methanol (19:1), there is eluted 3-[3-{4-[10,11-dihydro-3-methoxy-8-methyl-dibenz[b,f]oxepin-10-yl]-1-piperazinyl}-propyl]-2-oxazolidinone as an oily substance. This is converted, in acetone with maleic acid, to the 3-[3-{4-[10,11-dihydro-3-methoxy-8-methyl-dibenz[b,f]oxepin-10-yl]-1-piperazinyl}-propyl]-2-oxazolidinone-(1:2)-maleate having a melting point of 149°–151° C.

The 1-[10,11-dihydro-3-methoxy-8-methyl-dibenz[b,f]oxepin-10-yl]piperazine used as the starting material can be prepared as follows:

150 G. of 4-methoxy-anthranilic acid are suspended in 1 liters of water and 80 ml. of concentrated hydrochloric acid at 0° C. To this suspension is added dropwise over a period of 30 minutes, with stirring at 0°–5° C, a solution of 62 g. of sodium nitrite in 130 ml. of water. The resulting diazonium salt solution is stirred for an additional 15 minutes at 0°–5° C. A solution of 164 g. of potassium iodide in 700 ml. of 5-N sulfuric acid is subsequently added dropwise at 3°–6° C. over a period of 45 minutes. The mixture is stirred at room temperature for 30 minutes and subsequently slowly heated to reflux. After boiling for 2 hours at reflux, the mixture is cooled to room temperature. The separated brown crystals are removed by filtration and washed neutral with water. The filter cake is dried under reduced pressure and there is obtained 2-iodo-4-methoxy-benzoic acid as brown crystals which melt at 174° C. Then, the 2-iodo-4-methoxy-benzoic acid is converted in the manner described in Example 1 to give the desired starting material, 1-[10,11-dihydro-3-methoxy-8-methyl-dibenz[b,f]oxepin-10-yl]piperazine, in the form of an oil. The following intermediates are obtained:

4-methoxy-2-(4-methyl-phenoxy)-benzoic acid having a melting point of 156°–157° C;

4-methoxy-2-(4-methyl-phenoxy)-benzyl alcohol (oil);

1-chloromethyl-4-methoxy-2-(4-methyl-phenoxy)-benzene (oil);

4-methoxy-2-(4-methyl-phenoxy)-phenylacetonitrile (oil);

4-methoxy-2-(4-methyl-phenoxy)-phenylacetic acid (crystals);

10,11-dihydro-3-methoxy-8-methyl-dibenz[b,f]oxepin-10-one (oil);

4-[3-methoxy-8-methyl-dibenz[b,f]oxepin-10-yl]-1-piperazinecarboxylic acid ethyl ester (oil);

4-[10,11-dihydro-3-methoxy-8-methyl-dibenz[b,f]oxepin-10-yl]-1-piperazinecarboxylic acid ethyl ester (oil).

EXAMPLE 6

Preparation of
3-[2-{4-[2-chloro-10,11-dihydro-dibenz[b,f]oxepin-10-yl]-1-piperazinyl}-ethyl]-2-oxazolidinone 8.5 G. of 1-[2-chloro-10,11-dihydro-dibenz[b,f]oxepin-10-yl]-piperazine are stirred at reflux for 4 hours together with 8.1 g. of 3-(2-chloro-ethyl)-2-oxazolidinone, 2.95 g. of sodium carbonate and 0.4 g. of sodium iodide in 50 ml. of butanol. Then, the solvent is evaporated under reduced pressure and the residue partitioned between water and chloroform. The organic phase is washed with water, dried over sodium sulfate and evaporated under reduced pressure. The residue is recrystallized from methanol, and there is obtained 3-[2-{4-[2-chloro-10,11-dihydro-dibenz[b,f]oxepin-10-yl]-1-piperazinyl}-ethyl]-2-oxazolidinone having a melting point of 159°–160° C. The maleate, prepared in acetone, melts at 175°–177° C. (with decomposition). The dihydrochloride hydrate, prepared in ethanol, melts at 179°–181° C. (with decomposition).

The 1-[2-chloro-10,11-dihydro-dibenz[b,f]oxepin-10-yl]-piperazine used as the starting material can be prepared as follows:

52.5 G. of 10,11-dihydro-2-nitro-dibenz[b,f]oxepin-10-one are suspended in 900 ml. of ethyl acetate and 450 ml. of ethanol and hydrogenated in the presence of 300 mg. of platinum oxide at room temperature and normal pressure. The catalyst is removed by filtration, the filtrate evaporated in vacuo. The residue is crystallized from benzene/hexane, and there is obtained 2-amino-10,11-dihydro-dibenz[b,f]oxepin-10-one having a melting point of 116°–117° C.

26.4 G. of 2-amino-10,11-dihydro-dibenz[b,f]oxepin-10-one are dissolved in 230 ml. of 2-N aqueous methanesulfonic acid. The mixture is cooled to 0° C. There is added dropwise thereto over a period of 7 minutes a solution of 10.7 g. of sodium nitrite in 37.5 ml. of water in such a manner that the temperature does not exceed 5° C. The mixture is stirred for an additional 5 minutes at 5° C. Then, this solution of the diazonium methanesulfonate is poured into a mixture of 500 ml. of ethyl acetate and a solution of 37.5 g. of copper (I) chloride in 450 ml. of concentrated hydrochloric acid. The resulting mixture is stirred for an additional 10 minutes at room temperature and the phases are then separated. The ethyl acetate solution is washed several times with saturated aqueous sodium chloride solution, dried over sodium sulfate and evaporated in vacuo. The residue is dissolved in benzene and chromatographed over 400 g. of silica gel. Upon elution with benzene, there is obtained a substance which is crystallized from a small amount of isopropanol and there is obtained 2-chloro-10,11-dihydro-dibenz[b,f]oxepin-10-one having a melting point of 60°–61° C.

The desired starting material, 1-[2-chloro-10,11-dihydro-dibenz[b,f]oxepin-10-yl]-piperazine having a melting point of 85°–87° C., can be prepared from 2-chloro-10,11-dihydro-dibenz[b,f]oxepin-10-one in the manner described in Example 1, via the following intermediates:

4-[2-chloro-dibenz[b,f]oxepin-10-yl]-1-piperazinecarboxylic acid ethyl ester having a melting point of 139°–141° C;

4-[2-chloro-10,11-dihydro-dibenz[b,f]oxepin-10-yl]-1-piperazinecarboxylic acid ethyl ester having a melting point of 90°–92° C.

EXAMPLE 7

In an analogous manner to that described in Example 6, from 1-[2-chloro-10,11-dihydro-dibenz[b,f]oxepin-10-yl]-piperazine and 1-(2-chloro-ethyl)-2-pyrrolidinone, there is obtained 1-[2-{4-[2-chloro-10,11-dihydro-dibenz[b,f]oxepin-10-yl]-1-piperazinyl}-ethyl]-2-pyrrolidinone having a melting point of 120°–121° C. [the dihydrochloride, prepared in ethanol, melts at 222°–223° C. (with decomposition)];

from 1-[2-chloro-10,11-dihydro-dibenz[b,f]oxepin-10-yl]-piperazine and 1-(2-chloro-ethyl)-2-piperidone, there is obtained 1-[2-{4-[2-chloro-10,11-dihydro-dibenz[b,f]oxepin-10-yl]-1-piperazinyl}-ethyl]-2-piperidone [the dihydrochloride, prepared in ethanol, melts at 220°–222° C (with decomposition)];

from 1-[2-chloro-10,11-dihydro-dibenz[b,f]oxepin-10-yl]-piperazine and 1-(2-chloro-ethyl)-3-methyl-imidazolidinone, there is obtained 1-[2-{4-[2-chloro-10,11-dihydro-dibenz[b,f]oxepin-10-yl]-1-piperazinyl}-ethyl]-3-methyl-2-imidazolidinone, having a melting point of 119°–121° C. [the hydrochloride, prepared in water, melts at 200°–202° C. (with decomposition)]; and from 1-[10,11-dihydro-3-methoxy-8-methyl-dibenz[b,f]oxepin-10-yl]-piperazine and 3-(2-chloro-ethyl)-2-oxazolidinone, there is obtained 3-[2-{4-[10,11-dihydro-3-methoxy-8-methyl-dibenz[b,f]oxepin-10-yl]-1-piperazinyl}-ethyl]-2-oxazolidinone as an oil [the dihydrochloride, prepared in ethanol, melts at 183°–186° C (with decomposition)].

EXAMPLE 8

Preparation of 3-[2-{4-[2-bromo-10,11-dihydro-dibenz[b,f]oxepin-10-yl]-1-piperazinyl}-ethyl]-2-oxazolidinone In an analogous manner to that described in Example 6, from 1-[2-bromo-10,11-dihydro-dibenz[b,f]oxepin-10-yl]-piperazine and 3-(2-chloro-ethyl)-2-oxazolidinone, there is obtained 3-[2-{4-[2-bromo-10,11-dihydro-dibenz[b,f]oxepin-10-yl]-1-piperazinyl}-ethyl]-2-oxazolidinone having a melting point of 150°–152° C. The dihydrochloride, prepared in ethanol, melts at 175°–176° C.

The 1-[2-bromo-10,11-dihydro-dibenz[b,f]oxepin-10-yl]-piperazine used as the starting material can be prepared as follows:

In an analogous manner to that described in Example 6, 30 g. of 2-amino-10,11-dihydro-dibenz[b,f]oxepin-10-one are diazotized with 12 g. of sodium nitrite in methanesulfonic acid solution. The solution obtained is poured into a mixture of 540 ml. of ethyl acetate and a solution of 57.2 g. of copper (I) bromide in 666 ml. of 48% hydrobromic acid. After 10 minutes, the mixture is worked-up in the same manner as described in Example 6, and there is obtained 2-bromo-10,11-dihydro-dibenz[b,f]oxepin-10-one having a melting point of 53°–54° C. The product is reacted further in an analogous manner to that described in Example 1 to give the desired starting material, 1-[2-bromo-10,11-dihydro-dibenz[b,f]oxepin-10-yl]-piperazine having a melting point of 93°–94° C. The following intermediates are obtained:

4-[2-bromo-dibenz[b,f]oxepin-10-yl]-1-piperazinecarboxylic acid ethyl ester having a melting point of 168°–170° C;

4-[2-bromo-10,11-dihydro-dibenz[b,f]oxepin-10-yl]-1-piperazinecarboxylic acid ethyl ester having a melting point of 94°–95° C.

EXAMPLE 9

In an analogous manner to that described in Example 5, from 1-[2-chloro-10,11-dihydro-dibenz[b,f]oxepin-10-yl]-piperazine and 3-chloro-1-propanol, there is obtained 3-{4-[2-chloro-10,11-dihydro-dibenz[b,f]oxepin-10-yl]-1-piperazinyl}-1-propanol as an oil. The dihydrochloride, prepared in ethanol, melts at 206°–207° C (with decomposition).

EXAMPLE 10

Preparation of the palmitic acid ester of 3-{4-[2-chloro-10,11-dihydro-dibenz[b,f]oxepin-10-yl]-1-piperazinyl}-1-propanol 0.8 G. of 3-{4-[2-chloro-10,11-dihydro-dibenz[b,f]oxepin-10-yl]-1-piperazinyl}-1-propanol are dissolved in 5 ml. of pyridine. A solution of 0.6 g. of palmitic acid chloride in 2 ml. of benzene is added dropwise thereto with cooling and the mixture stirred for 20 hours at room temperature. The solvent is then evaporated under reduced pressure and the residue dissolved in benzene. The solution is chromatographed over 30 g. of silica gel. Elution is carried out first with benzene and subsequently with benzene/methanol (99:1). The palmitic acid ester of 3-{4-[2-chloro-10,11-dihydro-dibenzo[b,f]oxepin-10-yl]-1-piperazinyl}-1-propanol is eluted with benzene/methanol (97.3). This ester is obtained as an oil which is converted in acetone with maleic acid to the crystalline maleate having a melting point of 103°–105° C (with decomposition).

EXAMPLE 11

Preparation of the hydrochloride of 3-{4-[2-chloro-10,11-dihydro-dibenz[b,f]oxepin-10-yl]-1-piperazinyl}-propionic acid nitrile 10 G. of 1-[2-chloro-10,11-dihydro-dibenz[b,f]oxepin-10-yl]-piperazine are heated in 2.3 ml. of acrylic acid nitrile for 4 hours at 90° C. Then, the excess acrylic acid nitrile is evaporated under reduced pressure. The residue is reacted in ethanol with 1 equivalent of hydrogen chloride. The hydrochloride of 3-{4-[2-chloro-10,11-dihydro-dibenz[b,f]oxepin-10-yl]-1-piperazinyl}-propionic acid nitrile is removed by filtration and recrystallized from ethanol; melting point 187°–189° C (with decomposition).

EXAMPLE 12

Preparation of 4-{4-[2-chloro-10,11-dihydro-dibenz[b,f]oxepin-10-yl]-1-piperazinyl}-2-butyn-1-ol hydrochloride 6 G. of 1-[2-chloro-10,11-dihydro-dibenz[b,f]oxepin-10-yl]-piperazine are dissolved in 65 ml. of ethanol. Subsequently, there are added successively 2.7 g. of sodium carbonate, 0.27 g. of sodium iodide. Then, a solution of 2.4 g. of 4-chloro-2-butyn-1-ol in 15 ml. of ethanol is added dropwise. The mixture is stirred for 16 hours at room temperature and thereafter for 3.5 hours at 40° C. The ethanol is then evaporated under reduced pressure and the residue partitioned between water and chloroform. The phases are separated, the aqueous solution is extracted with water and the chloroform extracts are washed with water. The solvent is evaporated, the residue dissolved in benzene and chromatographed over 140 g. of silica gel. Elution is carried out first with benzene. The 4-{4-[2-chloro-10,11-dihydro-dibenz[b,-f]oxepin-10-yl]-1-piperazinyl}-2-butyn-1-ol is eluted with benzene/methanol (99:1), which is obtained as an oil and is converted to the hydrochloride using the calculated amount of hydrogen chloride in ethanol. The hydrochloride crystallizes by the addition of ether; melting point 194°–195° C. (with decomposition).

EXAMPLE 13

Preparation of 1-[2,8-dichloro-10,11-dihydro-dibenz[b,f]oxepin-10-yl]-4-(2-(propynyl)-piperazine 2.87 G. of sodium carbonate are added to a solution of 7.6 g. of 1-[2,8-dichloro-10,11-dihydro-dibenz[b,f]oxepin-10-yl]-piperazine in 76 ml. of ethanol. Then, a solution of 1.9 ml. of propargyl bromide in 15 ml. of ethanol is added dropwise with stirring. The mixture is stirred for 20 hours at room temperature and the solvent is then evaporated under reduced pressure. The residue is partitioned between water and chloroform. The phases are separated. The aqueous solution is extracted again with chloroform. The chloroform solutions are washed with water, dried over sodium sulfate and evaporated under reduced pressure. The residue is crystallized using diisopropyl ether, and there is obtained 1-[2,8-dichloro-10,11-dihydro-dibenz[b,f]oxepin-10-yl]-4-(2-propynyl)-piperazine having a melting point of 105°–107° C. The dihydrochloride, prepared in ethanol, melts at 213°–215° C. (with decomposition).

EXAMPLE 14

Preparation of 1-[2-fluoro-10,11-dihydro-dibenz[b,f]oxepin-10-yl]-4-methylpiperazine dihydrochloride 6.15 G. of sodium borohydride are added in small portions over a period of 15 minutes to a solution of 12.3 g. of 1-[2-fluoro-dibenzo[b,f]oxepin-10-yl]-4-methylpiperazine in 185 ml. of glacial acetic acid with cooling in such a manner that the temperature does not exceed 25° C. The mixture is stirred for an additional 1 hour at room temperature and the acetic acid is then evaporated in vacuo. The residue is partitioned between 3-N sodium hydroxide solution and chloroform. The aqueous phase is separated and extracted again with chloroform. The chloroform extracts are washed three times with water, dried over sodium sulfate, evaporated in vacuo, and there is obtained 1-[2-fluoro-10,11-dihydro-dibenz[b,f]oxepin-10-yl]-4-methyl-piperazine as a crystalline residue. The dihydrochloride, prepared in ethanol, melts at 240°–241° C. (with decomposition).

In a manner analogous to that described in the preceding paragraph, from 1-[3-methoxy-8-methyl-dibenz[b,f]oxepin-10-yl]-4-methyl-piperazine, there is obtained 1-[10,11-dihydro-3-methoxy-8-methyl-dibenz[b,f]oxepin-10-yl]-4-methyl-piperazine. The dihydrochloride, prepared in methanol/ether, melts at 190°–193° C.

Similarly, there is obtained
from 3-[2-{4-[2,8-dimethyl-dibenz[b,f]oxepin-10-yl]-1-piperazinyl}-ethyl]-2-oxazolidinone the compound 3-[2-{4-[10,11-dihydro-2,8-dimethyl-dibenz[b,f]oxepin-10-yl]-1-piperazinyl}-ethyl]-2-oxazolidinone; melting point 175°–176° C; melting point of the dihydrochloride 183° C (with decomposition);

from 3-[2-{4-[8-fluoro-2-methyl-dibenz[b,f]oxepin-10-yl]-1-piperazinyl}-ethyl]-2-oxazolidinone the compound 3-[2-{4-[8-fluoro-10,11-dihydro-2-methyl-dibenz[b,f]oxepin-10-yl]-1-piperazino}-ethyl]-2-oxazolidinone; melting point 145°–147° C; melting point of the monohydrochloride 229°–230° C (with decomposition);

from 3-[2-{4-[2-chloro-dibenz[b,f]oxepin-10-yl]-1-piperazinyl}-ethyl]-2-oxazolidinone the compound 3-[2-{4-[2-chloro-10,11-dihydro-dibenz[b,f]oxepin-10-yl]-1-piperazinyl}-ethyl]-2-oxazolidinone; melting point 159°–160° C; melting point of the dihydrochloride hydrate 179°–181° C (with decomposition);

from 3-{4-[2-chloro-dibenz[b,f]oxepin-10-yl]-1-piperazinyl}-propionic acid nitrile the compound 3-{4-[2-chloro-10,11-dihydro-dibenz[b,f]oxepin-10-yl]-1-piperazinyl}-propionic acid nitrile; melting point 187°–189° C (with decomposition).

The 1-[2-fluoro-10,11-dibenz[b,f]oxepin-10-yl]-4-methyl-piperazine used as the starting material in the first paragraph of this Example can be prepared as follows:

10,11-Dihydro-2-nitro-dibenz[b,f]oxepin-10-one is hydrogenated in the manner described in Example 6 to give 2-amino-10,11-dihydro-dibenz[b,f]oxepin-10-one having a melting point of 116°–117° C.

33.75 G. of 2-amino-10,11-dihydro-dibenz[b,f]oxepin-10-one are dissolved in 375 ml. of 2-N aqueous methanesulfonic acid and the solution is cooled to 0° C. A solution of 13.5 g. of sodium nitrite in 45 ml. of water is added dropwise at −2° C. to 0° C. within 4 minutes with stirring and cooling. The mixture is stirred at 0° C. for an additional 5 minutes and then 75 ml. of 4.3-M aqueous sodium tetrafluoroborate solution are added. After 30 minutes, the precipitated diazonium tetrafluoroborate is removed by filtration, washed with methanol and ether and carefully dried over phosphorus pentoxide.

30 G. of the foregoing diazonium tetrafluoroborate are heated from the side with a gas flame in a flask flushed with a nitrogen stream. As soon as decomposition begins (at about 140° C.), the heating is stopped and the exothermal reaction is allowed to spread over the entire mass. Then, the mixture is heated to 190° C. for an additional 13 minutes. After cooling, the mixture is taken up in benzene. The insoluble fractions are removed by filtration and the filtrate is chromatographed over 300 g. of silica gel. Elution with benzene yields crude 2-fluoro-10,11-dihydro-dibenz[b,f]oxepin-10-one, which is distilled (boiling point 85°–89° C/0.03 Torr.) and then melts at 63°–64° C.

A solution of 6.44 g. of titanium (IV) chloride in 25 ml. of benzene is added dropwise over a period of 15 minutes with cooling to a solution of 9.12 g. of 2-fluoro-10,11-dihydro-dibenz[b,f]oxepin-10-one and 18 g. of 1-methyl-piperazine in 100 ml. of benzene in such a manner that the temperature does not exceed 25° C. The mixture is subsequently stirred for 4 hours at reflux. The resulting mixture is cooled and poured into a solution of 10 g. of sodium bicarbonate in 100 ml. of water. The precipitated titanium dioxide is removed by filtration and washed carefully with benzene and chloroform. The benzene solution and the chloroform solution are washed four times with water, combined, dried over sodium sulfate, evaporated in vacuo, and there is obtained crude, crystalline 1-[2-fluoro-dibenz[b,f]oxepin-10-yl]-4-methyl-piperazine.

EXAMPLE 15

Preparation of 1-[2-chloro-10,11-dihydro-dibenz[b,f]oxepin-10-yl]-4-methyl-piperazine dihydrochloride In an analogous manner to that described in Example 14, from 1-[2-chloro-dibenz[b,f]oxepin-10-yl]-4-methyl-piperazine there is obtained 1-[2-chloro-10,11-dihydro-dibenz[b,f]oxepin-10-yl]-4-methyl-piperazine. The dihydrochloride, prepared in ethanol, melts at 238°–240° C (with decomposition).

The 1-[2-chloro-dibenz[b,f]oxepin-10-yl]-4-methyl-piperazine having a melting point of 119°–120° C. [maleate: melting point 200°–202° C (with decomposition)] used as the starting material can be prepared in an analogous manner to that described in Example 14 from 2-chloro-10,11-dihydro-dibenz[b,f]oxepin-10-one and 1-methyl-piperazine.

EXAMPLE 16

Preparation of 1-[8-fluoro-10,11-dihydro-2-methyl-dibenz[b,f]oxepin-10-yl]-4-methyl-piperazine dihydrochloride 15 G. of 4-[8-fluoro-10,11-dihydro-2-methyl-dibenz[b,f]oxepin-10-yl]-1-piperazinecarboxylic acid ethyl ester are dissolved in 15 ml. of benzene. With stirring and cooling, 39 ml. of a 70% solution of sodium dihydro-bis(2-methoxyethoxy)-aluminate in benzene are added dropwise at a temperature of 20°–30° C. Then, the mixture is heated to 60° C. for 1 hour, again cooled and treated at 10°–15° C. with 60 ml. of 20% sodium hydroxide solution. The phases are separated. The aqueous phase is extracted two additional times with benzene. The benzene solutions are washed several times with saturated sodium chloride solution, dried over sodium sulfate and evaporated in vacuo. The residue is converted into the dihydrochloride with ethanolic hydrochloric acid, and there is obtained 1-[8-fluoro-10,11-dihydro-2-methyl-dibenz[b,f]oxepin-10-yl]-4-methyl-piperazine dihydrochloride which, after recrystallization from methanol/ether, melts at 235°–238° C. (with decomposition).

EXAMPLE 17

Preparation of 1-[10,11-dihydro-2,8-dimethyl-dibenz[b,f]oxepin-10-yl]-4-methyl-piperazine dihydrochloride 4-[10,11-Dihydro-2,8-dimethyl-dibenz[b,f]oxepin-10-yl]-1-piperazinecarboxylic acid ethyl ester is reacted with sodium dihydro-bis(2-methoxyethoxy)aluminate in the manner described in Example 16, and there is obtained 1-[10,11-dihydro-2,8-dimethyl-dibenz[b,f]oxepin-10-yl]-4-methyl-piperazine which is isolated as the dihydrochloride having a melting point of 197°–198° C. (with decomposition).

EXAMPLE 18

Preparation of 1-[2-chloro-8-fluoro-10,11-dihydro-dibenz[b,f]oxepin-10-yl]-4-methyl-piperazine dihydrochloride 4-[2-Chloro-8-fluoro-10,11-dihydro-dibenz[b,f]oxepin-10-yl]-1-piperazinecarboxylic acid ethyl ester is reacted with sodium dihydro-bis(2-methoxyethoxy)aluminate in an analogous manner to that described in Example 16, and there is obtained 1-[2-chloro-8-fluoro-10,11-dihydro-dibenz[b,f]oxepin-10-yl]-4-methylpiperazine which is isolated as the dihydrochloride having a melting point of 250° C. (with decomposition).

EXAMPLE 19

Preparation of 1-[10,11-dihydro-3-methoxy-8-methyl-dibenz[b,f]oxepin-10-yl]-4-(2-propynyl)-piperazine dihydrochloride 3.8 G. of sodium carbonate are added to a solution of 10 g. of 1-[10,11-dihydro-3-methoxy-8-methyl-dibenz[b,f]oxepin-10-yl]-piperazine in 55 ml. of butanol and then a solution of 2.5 ml. of propargyl bromide in 20 ml. of butanol is added dropwise. Then, the mixture is stirred for 20 hours at room temperature and the solvent is removed by distillation under reduced pressure. After working-up in an analogous manner to that described in Example 13, there is isolated crude 1-[10,11-dihydro-3-methoxy-8-methyl-dibenz[b,f]oxepin-10-yl]-4-(2-propynyl)piperazine in the form of an oil. The dihydrochloride, prepared in ethanol and recrystallized from methanol/ether, melts at 210°–212° C. (with decomposition).

EXAMPLE 20

Preparation of
10,11-dihydro-8-methyl-10-(4-methyl-1-piperazinyl)-dibenz[b,f]oxepin-3-ol dihydrobromide 4.0 G. of 4-[10,11-dihydro-3-methoxy-8-methyl-dibenz[b,f]oxepin-10-yl]-1-methyl-piperazine are dissolved in 600 ml. of methylene chloride, treated with a solution of 8.9 g. of boron tribromide in 90 ml. of methylene chloride and stirred at room temperature for 20 hours. The residue is taken up in 150 ml. of methanol, boiled at reflux for 30 minutes with active carbon, filtered, concentrated to about 70 ml., treated with ether until turbidity sets in, and there is obtained crystalline 10,11-dihydro-8-methyl-10-(4-methyl-1-piperazinyl)-dibenz[b,f]oxepin-3-ol dihydrobromide having a melting point of 176° C. (with decomposition).

EXAMPLE 21

Preparation of
1-[3-chloro-10,11-dihydro-7-trifluoromethyl-dibenz[b,f]oxepin-10-yl]-4-methyl-piperazine 11.9 G. of 1-[3-chloro-7-trifluoromethyl-dibenz[b,f]oxepin-10-yl]-4-methyl-piperazine was reduced with sodium borohydride in glacial acetic acid in a manner analogous to that described in Example 14, and there is obtained crude 1-[3-chloro-10,11-dihydro-7-trifluoromethyl-dibenz[b,f]oxepin-10-yl]-4-methyl-piperazine which is recrystallized from isopropanol and melts at 110° C. The dihydrochloride, prepared in ethanol, melts at 219°-222° C. (with decomposition).

The 1-[3-chloro-7-trifluoromethyl-dibenz[b,f]oxepin-10-yl]-4-methyl-piperazine used as the starting material can be prepared as follows:

In a manner analogous to that described in Example 1, 4-chloro-2-iodobenzoic acid is reacted with 3-trifluoromethyl-phenol, and there is obtained 4-chloro-2-(3-trifluoromethyl-phenoxy)-benzoic acid having a melting point of 146° C.

136 G. of 4-chloro-2-(3-trifluoromethyl-phenoxy)-benzoic acid are boiled at reflux for 2.5 hours in a mixture of 1000 ml. of methanol and 100 ml. of concentrated sulfuric acid. After concentration of the mixture under vacuum, the residue is poured on to ice and extracted with benzene. The benzene extracts are washed with water, aqueous sodium bicarbonate solution and again with water. After evaporation of the benzene, there is obtained 4-chloro-2-(3-trifluoromethyl-phenoxy)-benzoic acid methyl ester in the form of an oil.

A solution of 103 g. of 4-chloro-2-(3-trifluoromethyl-phenoxy)-benzoic acid methyl ester in 400 ml. of tetrahydrofuran is added dropwise at reflux over a period of 30 minutes to a solution of 16.2 g. of lithium borohydride in 280 ml. of absolute tetrahydrofuran. The mixture is then cooled to 0° C. and slowly added dropwise to 400 ml. of 3-N aqueous hydrochloric acid. After the addition of 500 ml. of water, the mixture is extracted twice with ether. After evaporation of the ether, there is obtained 4-chloro-2-(3-trifluoromethyl-phenoxy)-benzyl alcohol in the form of an oil.

Starting from the foregoing 4-chloro-2-(3-trifluoromethyl-phenoxy)-benzyl alcohol there are obtained, in a manner analogous to that described in Example 1, the following intermediates:

4-chloro-2-(3-trifluoromethyl-phenoxy)-benzyl chloride (oil);

4-chloro-2-(3-trifluoromethyl-phenoxy)-phenylacetonitrile (oil);

4-chloro-2-(3-trifluoromethyl-phenoxy)-phenylacetic acid having a melting point of 80° C;

3-chloro-10,11-dihydro-7-trifluoromethyl-dibenz[b,f]oxepin-10-one having a melting point of 108° C.

The last-named intermediate is reacted with 1-methylpiperazine in the same manner as described in Example 14 to give the desired starting material, 1-[3-chloro-7-trifluoromethyl-dibenz[b,f]oxepin-10-yl]-4-methylpiperazine, having a melting point of 170° C.

EXAMPLE 22

Preparation of
1-[2-{4-[10,11-dihydro-2-methyl-8-methylthio-dibenz[b,f]oxepin-10-yl]-1-piperazinyl}-ethyl]-2-piperidone dihydrochloride A solution of 3 g. of 10-chloro-10,11-dihydro-2-methyl-8-methylthio-dibenz[b,f]oxepin and 5.73 g. of 1-[2-(1-piperazinyl)-ethyl]-2-piperidone in 18 ml. of chloroform is heated at reflux for 20 hours. The solvent is removed in vacuo. The residue is partitioned between benzene and 10% aqueous sodium carbonate solution. The benzene solution is extracted with dilute hydrochloric acid. The acid-aqueous solution is made alkaline with sodium bicarbonate and extracted with benzene. The benzene extract is washed several times with water, dried, evaporated in vacuo, and there is obtained 1-[2-{4-[10,11-dihydro-2-methyl-8-methylthio-dibenz[b,f]oxepin-10-yl]-1-piperazinyl}-ethyl]-2-piperidone. The dihydrochloride is prepared in ethanol by the addition of an excess of alcoholic hydrogen chloride. By the addition of ether, there are obtained crystals having a melting point of 183°-185° C. (with decomposition). By re-dissolving the dihydrochloride in water, there is obtained the monohydrochloride having a melting point of 117°-120° C.

The 10-chloro-10,11-dihydro-2-methyl-8-methylthio-dibenz[b,f]oxepin used as the starting material is prepared as follows:

In a manner analogous to that described in Example 1, the following intermediates are prepared:

5-methyl-2-(4-methylthio-phenoxy)-benzoic acid having a melting point of 124°-125° C. (from 2-iodo-5-methyl-benzoic acid and 4-methylthio-phenol);

5-methyl-2-(4-methylthio-phenoxy)-benzyl alcohol (oil);

3-chloromethyl-4-(4-methylthio-phenoxy)-toluene (oil);

5-methyl-2-(4-methylthio-phenoxy)-phenylacetonitrile (oil);

5-methyl-2-(4-methylthio-phenoxy)-phenylacetic acid.

The foregoing acid is obtained in the form of a crude oil and is purified as follows:

47 g. of crude 5-methyl-2-(4-methylthio-phenoxy)-phenylacetic acid are dissolved in 170 ml. of methanol. 19 Ml. of concentrated sulfuric acid are added dropwise with stirring and the mixture is subsequently heated at reflux for 3.5 hours. After cooling, the mixture is diluted with water and extracted several times with benzene. The benzene extracts are washed with water, sodium bicarbonate solution and again with water. After evaporation of the solvent, there remains a residue which is chromatographed on 400 g. of silica gel. By elution with benzene, there is obtained 5-methyl-2-(4-methylthio-phenoxy)-phenylacetic acid methyl ester, which ester is dissolved in 73 ml. of methanol, treated with 18.8 g. of potassium hydroxide and 73 ml. of water and subsequently heated at reflux for 1 hour. Thereafter, the methanol is removed in vacuo and the residue acidified with hydrochloric acid. The mixture is extracted with benzene, the benzene extract washed with water and concentrated in vacuo. The residue is crystallized from cyclohexane, and there is obtained 5-methyl-2-(4-methylthio-phenoxy)-phenylacetic acid having a melting point of 81°–83° C.

By treatment of the foregoing acid with polyphosphoric acid in a manner analogous to that described in Example 1, there is obtained 10,11-dihydro-2-methyl-8-methylthio-dibenz[b,f]oxepin-10-one having a melting point of 102°–103° C.

8.9 G. of 10,11-dihydro-2-methyl-8-methylthio-dibenz[b,f]oxepin-10-one are suspended in 65 ml. of ethanol and treated with a solution of 1.25 g. of sodium borohydride in 4.3 ml. of water. The mixture is stirred for 2 hours at room temperature. Then, 20 ml. of methanol are added thereto and the resulting mixture is heated at reflux for 15 minutes. Thereafter, the methanol and ethanol are removed by evaporation in vacuo. The residue is extracted with chloroform, the chloroform extracts are washed with water, dried and evaporated in vacuo. The residue is crystallized from diisopropyl ether, and there is obtained 10,11-dihydro-3-methyl-8-methylthio-dibenz[b,f]oxepin-10-ol having a melting point of 67°–69° C.

7.5 G. of 10,11-dihydro-3-methyl-8-methylthio-dibenz[b,f]oxepin-10-one are dissolved in 75 ml. of benzene. 7.5 G. of anhydrous calcium chloride are added thereto and the mixture is saturated with hydrogen chloride. Then, the resulting mixture is stirred at room temperature for 16 hours and filtered. The filtrate is evaporated in vacuo and there is obtained 10-chloro-10,11-dihydro-3-methyl-8-methylthio-dibenz[b,f]oexpin.

EXAMPLE 23

Preparation of 1-[10,11-dihydro-2,8-dimethyl-dibenz[b,f]oxepin-10-yl]-4-allyl-piperazine dihydrochloride A solution of 8.3 g. of 1-[10,11-dihydro-2,8-dimethyl-dibenz[b,f]oxepin-10-yl]-piperazine in 90 ml. of ethanol is treated with 3.55 g. of sodium carbonate. Then, a solution of 2.3 ml. of allyl bromide in 19 ml. of ethanol is added dropwise with stirring over a period of 10 minutes. The resulting mixture is stirred for an additional 100 minutes and then the solvent is evaporated in vacuo. The residue is partitioned between water and chloroform. The chloroform phase is evaporated in vacuo. The residue is dissolved in benzene and chromatographed over 200 g. of silica gel. Impurities are first removed by elution with benzene. The oily 1-[10,11-dihydro-2,8-dimethyl-dibenz[b,f]oxepin-10-yl]-4-allyl-piperazine is eluted with a mixture of 98% benzene and 2% methanol. The dihydrochloride, prepared in ethanol, melts at 219°–221° C. (with decomposition).

EXAMPLE 24

Preparation of 1-[10,11-dihydro-2,8-dimethyl-dibenz[b,f]-oxepin-10-yl]-4-methyl-piperazine dihydrochloride 0.8 G. of 10-chloro-10,11-dihydro-2,8-dimethyl-dibenz[b,f]oxepin and 0.58 g. of 1-methyl-piperazine are dissolved in 4 ml. of chloroform and heated at reflux for 21 hours. Then, the chloroform is evaporated in vacuo. The residue is partitioned between benzene and aqueous sodium carbonate solution. The benzene solution is extracted with dilute hydrochloric acid. The hydrochloric acid extract is made alkaline with sodium carbonate and extracted with benzene. Thereafter, the benzene extract is washed several times with water, dried over sodium sulfate, evaporated in vacuo, and there is obtained 1-[10,11-dihydro-2,8-dimethyl-dibenz[b,f]oxepin-10-yl]-4-methyl-piperazine, the dihydrochloride of which melts at 197°–198° C. (with decomposition).

In a manner analogous to that described in the preceding paragraph, by reacting 10-chloro-10,11-dihydro-2,8-dimethyl-dibenz[b,f]oxepin with 3-[2-(1-piperazinyl)-ethyl]-2-oxazolidinone there is obtained 3-[2-{4-[10,11-dihydro-2,8-dimethyl-dibenz[b,f]oxepin-10-yl]-1-piperazinyl}-ethyl]-2-oxazolidinone having a melting point of 175°–176° C.

Similarly, there is obtained
from 10-chloro-8-fluoro-10,11-dihydro-2-methyl-dibenz[b,f]oxepin and 3-[2-(1-piperazinyl)-ethyl]-2-oxazolidinone the compound 3-[2-{4-[8-fluoro-10,11-dihydro-2-methyl-dibenz[b,f]oxepin-10-yl}-1-piperazino}-ethyl]-2-oxazolidinone; melting point 145°–147° C; melting point of the monohydrochloride 229°–230° C (with decomposition);
from 2,10-dichloro-10,11-dihydro-dibenz[b,f]oxepin and 3-[(1-piperazinyl)-ethyl]-2-oxazolidinone the compound 3-[2-{4-[2-chloro-10,11-dihydro-dibenz[b,f]oxepin-10-yl]-1-piperazinyl}-ethyl]-2-oxazolidinone; melting point 159°–160° C; melting point of the dihydrochloride hydrate 179°–181° C (with decomposition);
from 2,10-dichloro-10,11-dihydro-dibenz[b,f]oxepin and 3-(1-piperazinyl)-propionic acid nitrile the compound 3-{4-[2-chloro-10,11-dihydro-dibenz[b,f]oxepin-10-yl]-1-piperazinyl}-propionic acid nitrile; melting point of the dihydrochloride 187°–189° C (with decomposition).

The 10-chloro-10,11-dihydro-2,8-dimethyl-dibenz[b,f]oxepin used as the starting material can be prepared in a manner analogous to that described in Example 22 from 10,11-dihydro-2,8-dimethyl-dibenz[b,f]oxepin-10-one by reduction to form 10,11-dihydro-2,8-dimethyl-dibenz[b,f]oxepin-10-ol having a melting point of 73.5°–74° C. and subsequent treatment with hydrogen chloride in the presence of calcium chloride. Analogous procedures apply to the manufacture of 10-chloro-8-fluoro-10,11-dihydro-2-methyl-dibenz[b,f]oxepin and 2,10-dichloro-10,11-dihydro-dibenz[b,f]oxepin.

The following Examples illustrate pharmaceutical preparations containing the representative dibenz[b,f]oxepin derivatives of the invention:

EXAMPLE A

| Tablets | Per Tablet |
|---|---|
| 3-[2-{4-[10,11-Dihydro-2,8-dimethyl-dibenz[b,f]oxepin-10-yl]-1-piperazinyl}-ethyl]-2-oxazolidinone | 100 mg. |
| Lactose | 202 mg. |
| Maize Starch | 80 mg. |
| Hydrolyzed maize starch | 20 mg. |
| Calcium stearate | 8 mg. |
| Total Weight | 410 mg. |

The 3-[2-{4-[10,11-dihydro-2,8-dimethyl-dibenz[b,f]oxepin-10-yl]-1-piperazinyl}-ethyl]-2-oxazolidinone, lactose, maize starch and hydrolyzed maize starch are mixed together and granulated with water to form a viscous paste. This paste is passed through a sieve and subsequently dried at 45° C. overnight. The dried granulate is passed through a sieve and, thereafter, mixed with the calcium stearate. The mixture obtained is pressed into tablets each weighing 410 mg. and having a diameter of about 10 mm.

EXAMPLE B

| Tablets | Per Tablet |
|---|---|
| 3-[2-{4-[10,11-Dihydro-2,8-dimethyl-dibenz[b,f]oxepin-10-yl]-1-piperazinyl}-ethyl]-2-oxazolidinone | 25.0 mg. |
| Lactose | 114.0 mg. |
| Maize Starch | 50.0 mg. |
| Gelatinized maize starch | 8.0 mg. |
| Calcium stearate | 3.0 mg. |
| Total Weight | 200.0 mg. |

The 3-[2-{4-[10,11-dihydro-2,8-dimethyl-dibenz[b,f]oxepin-10-yl]-1-piperazinyl}-ethyl]-2-oxazolidinone, lactose, maize starch and gelatinized maize starch are intimately mixed with one another. The mixture is passed through a comminuting machine and moistened with water to give a thick paste. The moist mass is passed through a sieve. The moist granulate is thereafter dried at 45° C. The dried granulate is thoroughly mixed with the calcium stearate. Then, the granulate is pressed to tablets each weighing 200 mg. and having a diameter of ca. 8 mm.

EXAMPLE C

| Tablets | Per Tablet |
|---|---|
| 3-[2-{4-[10,11-Dihydro-2,8-dimethyl-dibenz[b,f]oxepin-10-yl]-1-piperazinyl}-ethyl]-2-oxazolidinone dihydrochloride | 14.5 mg. |
| Lactose | 124.5 mg. |
| Maize Starch | 50.0 mg. |
| Gelatinized maize starch | 8.0 mg. |
| Calcium stearate | 3.0 mg. |
| Total Weight | 200.0 mg. |

The 3-[2-{4-[10,11-dihydro-2,8-dimethyl-dibenz[b,f]oxepin-10-yl]-1-piperazinyl}-ethyl]-2-oxazolidinone dihydrochloride, lactose, maize starch and gelatinized maize starch are intimately mixed with one another. The mixture is passed through a comminuting machine and subsequently moistened with water to give a thick paste. The moist mass is passed through a sieve. The moist granulate is dried at 45° C. The dried granulate is thoroughly mixed with the calcium stearate. Thereafter, the granulate is pressed into tablets each weighing 200 mg. and having a diameter of ca. 8 mm.

EXAMPLE D

| Tablets | Per Tablet |
|---|---|
| 3-[2-{4-[10,11-Dihydro-2,8-dimethyl-dibenz[b,f]oxepin-10-yl]-1-piperazinyl}-ethyl]-2-oxazolidinone | 25.00 mg. |
| Lactose | 110.00 mg. |
| Maize starch | 61.00 mg. |
| Talc | 3.40 mg. |
| Magnesium stearate | 0.60 mg. |
| Total Weight | 200.00 mg. |

The ingredients are intimately mixed with one another and pressed to tablets each weighing 200 mg. The tablets are subsequently coated with ethylcellulose and Carbowax.

EXAMPLE E

| Capsules | Per Capsule |
|---|---|
| 3-[2-{4-[10,11-Dihydro-2,8-dimethyl-dibenz[b,f]oxepin-10-yl]-1-piperazinyl}-ethyl]-2-oxazolidinone hydrochloride | 29.0 mg. |
| Lactose | 156.0 mg. |
| Maize starch | 30.0 mg. |
| Talc | 5.0 mg. |
| Total content | 220.0 mg. |

The 3-[2-{4-[10,11-dihydro-2,8-dimethyl-dibenz[b,f]oxepin-10-yl]-1-piperazinyl}-ethyl]-2-oxazolidinone hydrochloride, lactose and maize starch are intimately mixed with one another and passed through a comminuting machine. The mixture is then thoroughly mixed with the talc and filled into hard-shell gelatin capsules.

EXAMPLE F

| Capsules | Per Capsule |
|---|---|
| 3-[2-{4-[10,11-Dihydro-2,8-dimethyl-dibenz[b,f]oxepin-10-yl]-1-piperazinyl}-ethyl]-2-oxazolidinone | 25.5 mg. |
| Lactose | 159.5 mg. |
| Maize starch | 30.0 mg. |
| Talc | 5.0 mg. |
| Total content | 220.0 mg. |

The 3-[2-{4-[10,11-dihydro-2,8-dimethyl-dibenz[b,f]oxepin-10-yl]-1-piperazinyl}-ethyl]-2-oxazolidinone, lactose and maize starch are intimately mixed with one another and passed through a comminuting machine. The mixture is thoroughly mixed with the talc and thereafter filled into hard-shell gelatin capsules.

EXAMPLE G

| Parenteral Formulation | |
|---|---|
| Each 1 ml. ampul contains the following ingredients: | |
| 3-[2-{4-[10,11-Dihydro-2,8-dimethyl-dibenz[b,f]oxepin-10-yl]-1-piperazinyl}-ethyl]-2-oxazolidinone | 10.20 mg. (2% excess) |
| Methanesulfonic acid for injection purposes | 2.22 mg. |
| Glucose for injection purposes | 40.0 mg. |
| Water for injection purposes q.s. ad | 1 ml. |

22.2 G. of methanesulfonic acid for injection purposes, 102 g. of 3-[2-{4-[10,11-dimethyl-dibenz[b,f]oxepin-10-yl]-1-piperazinyl}-ethyl]-2-oxazolidinone and 400 g. of glucose are successively dissolved in 8000 ml. of water for injection purposes in a glass vessel with stirring at room temperature. Then, water for injection purposes is added to provide a total volume of 10,000 ml. The solution is either filtered sterile and filled into colorless ampuls which are gassed with nitrogen and sealed or filled into colorless ampuls which are gassed with nitrogen, sealed and then sterilized with a stream of steam or autoclaved at 120° C.

EXAMPLE H

In place of the active ingredients used in Examples A–G, there can also be used other dibenz[b,f]oxepin derivatives of the invention, for example:

3-[2-{4-[8-fluoro-10,11-dihydro-2-methyl-dibenz[b,-f]oxepin-10-yl]-1-piperazinyl}-ethyl]-2-oxazolidinone or the dihydrochloride thereof;

3-[2-{4-[2-chloro-10,11-dihydro-dibenz[b,f]oxepin-10-yl]-1-piperazinyl}-ethyl]-2-oxazolidinone or the maleate thereof;

3-{3-[2-chloro-10,11-dihydro-dibenz[b,f]-oxepin-10-yl]-1-piperazinyl}-propionic acid nitrile or the hydrochloride thereof.

We claim:
1. A compound of the formula

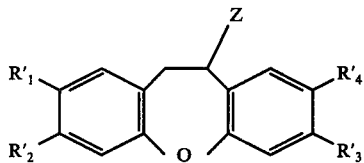

wherein Z is a leaving atom or group selected from the group consisting of halogen, alkyl-substituted sulfonyloxy and aryl-substituted sulfonyloxy; $R'_1$ is methyl and $R'_2$ is hydrogen; $R'_3$ is hydrogen and $R'_4$ is fluoro.

2. A compound in accordance with claim 1 in which Z is chloro, i.e. 10-chloro-8-fluoro-10,11-dihydro-2-methyl-dibenz[b,f]oxepin.

* * * * *